United States Patent [19]
Mullins et al.

[11] Patent Number: 5,859,430
[45] Date of Patent: Jan. 12, 1999

[54] METHOD AND APPARATUS FOR THE DOWNHOLE COMPOSITIONAL ANALYSIS OF FORMATION GASES

[75] Inventors: Oliver C. Mullins, Ridgefield; Xu Wu, Danbury, both of Conn.

[73] Assignee: Schlumberger Technology Corporation, Ridgefield, Conn.

[21] Appl. No.: 827,647

[22] Filed: Apr. 10, 1997

[51] Int. Cl.⁶ ............................. G01N 21/35; G01N 33/24
[52] U.S. Cl. ........................... 250/255; 250/256; 250/343; 250/339.13
[58] Field of Search .............................. 250/253, 255, 250/256, 269.1, 343, 345, 347, 339.13

[56] References Cited

U.S. PATENT DOCUMENTS

| | | | |
|---|---|---|---|
| 3,743,426 | 7/1973 | Steinberg | 250/345 |
| 3,780,575 | 12/1973 | Urbanosky | 73/152 |
| 3,859,851 | 1/1975 | Urbanosky | 73/155 |
| 4,336,453 | 6/1982 | Imaki et al. | 250/344 |
| 4,496,840 | 1/1985 | Fabinski et al. | 250/345 |
| 4,567,366 | 1/1986 | Shinohara | 250/339.13 |
| 4,609,821 | 9/1986 | Summers | 250/255 |
| 4,620,284 | 10/1986 | Schnell | 364/498 |
| 4,684,805 | 8/1987 | Shu-Ti Lee et al. | 250/345 |
| 4,770,243 | 9/1988 | Fouillout et al. | |
| 4,771,176 | 9/1988 | Schiefer et al. | 250/339.13 |
| 4,829,183 | 5/1989 | McClatchie et al. | 250/345 |
| 4,994,671 | 2/1991 | Safinya | 250/255 |
| 5,166,747 | 11/1992 | Schroeder et al. | 250/256 |
| 5,167,149 | 12/1992 | Mullins | 73/155 |
| 5,201,220 | 4/1993 | Mullins | 73/155 |
| 5,214,593 | 5/1993 | Magnussen, Jr. et al. | |
| 5,285,071 | 2/1994 | LaCount | 250/343 |
| 5,331,156 | 7/1994 | Hines | 250/256 |
| 5,412,581 | 5/1995 | Tackett | 250/343 |
| 5,464,982 | 11/1995 | Drucker et al. | 250/339.13 |
| 5,510,269 | 4/1996 | Black et al. | 250/339.13 |
| 5,689,114 | 11/1997 | Miyazaki et al. | 250/343 |

FOREIGN PATENT DOCUMENTS

| | | |
|---|---|---|
| 0 145 877A | 6/1985 | European Pat. Off. |
| 28 10 117 | 9/1979 | Germany |
| 33 40 505 A | 5/1985 | Germany |

OTHER PUBLICATIONS

"Effect of high pressure on the optical detection of gas by index of refraction methods" by Mullins et al., Applied Optics, vol. 33, No. 34, Dec. 1, 1994, pp. 7963–7970.

Primary Examiner—Edward J. Glick
Assistant Examiner—Darren M. Jiron
Attorney, Agent, or Firm—David P. Gordon; Keith G. W. Smith

[57] ABSTRACT

A borehole tool analyzes the composition of gases flowing from a formation. The tool includes an optical fluid analyzer (OFA) and a gas analysis module (GAM). The OFA determines when fluid flowing into the tool has become substantially only gas. The gas is then diverted to the GAM, thereby avoiding the possibility of oil depositing itself on a optical window and interfering with a proper analysis. The GAM includes a near infrared ray light source, at least one photo-detector, a gas sample cell (or cells) having portions with different path lengths, each portion having an optical window, and fiber optics which direct light in first paths from the source to the sample cell, and from the sample cell to the photo-detectors. By providing cells with different path lengths, issues of dynamic range are obviated. The GAM also preferably includes a second optical path which goes directly from the light source to the photo-detectors and is used for canceling drift, and a third optical path which goes from the light source, through a known standard such as methane to the photo-detectors and is used for compensation of shifts in actual hydrocarbon peak locations or shifts in optical filter wavelengths. Analysis of the different hydrocarbon gas components of the gas stream is conducted by analysis of selected CH vibrational peaks in the 5700 cm$^{-1}$ to 6100 cm$^{-1}$ range.

20 Claims, 8 Drawing Sheets

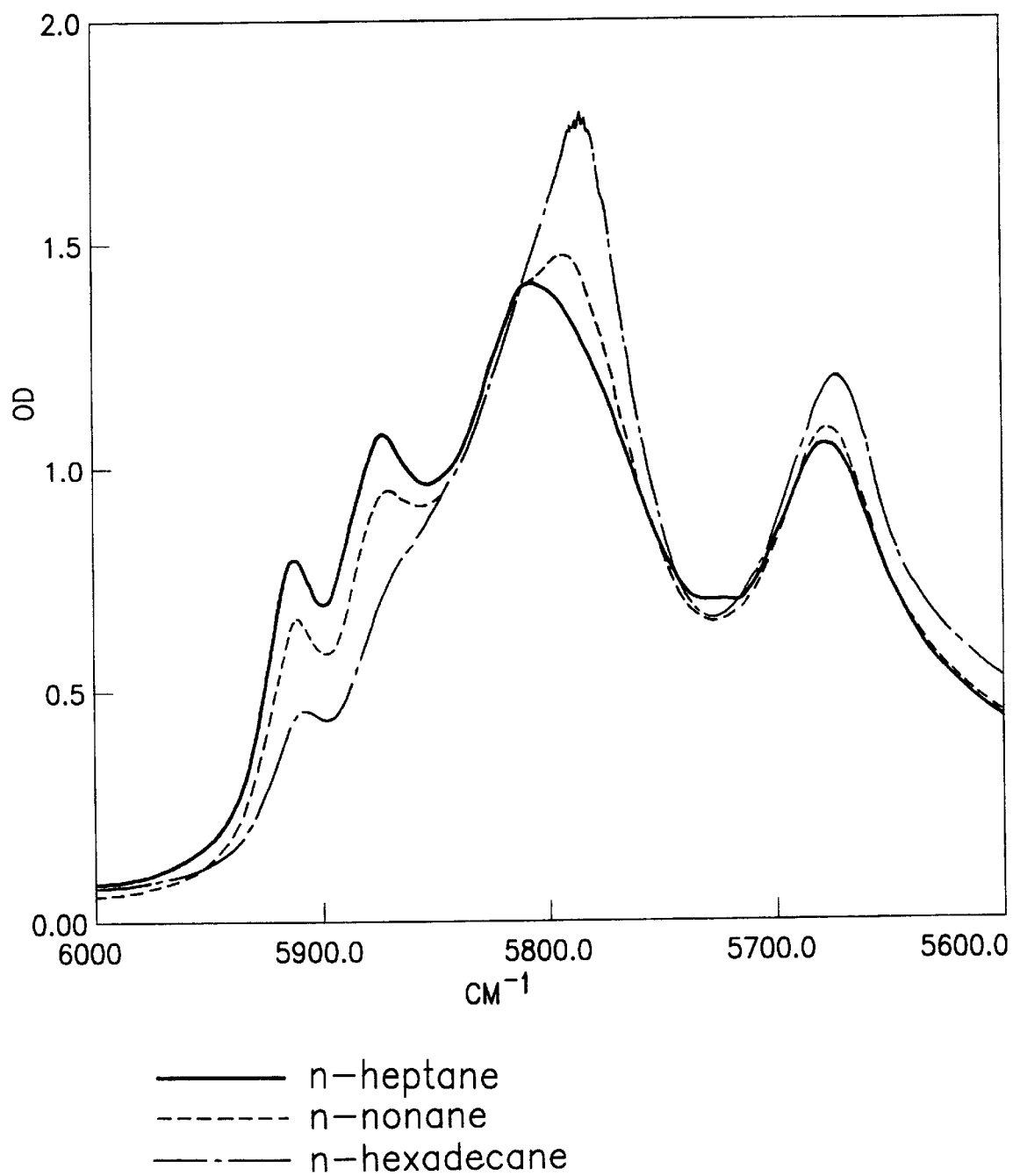

METHOD AND APPARATUS FOR THE DOWNHOLE COMPOSITIONAL ANALYSIS OF FORMATION GASES

BACKGROUND OF THE INVENTION

The present invention is related to co-owned U.S. Pat. No. 4,994,671 to Safinya et al., No. 5,167,149 to Mullins et al., 5,201,220 to Mullins et al., No. 5,266,800 to Mullins et al., and No. 5,331,156 to Hines et al., all of which are hereby incorporated by reference herein in their entireties.

1. Field of the Invention

The present invention relates to the analysis of downhole borehole fluids. More particularly, the present invention relates to apparatus and methods for the downhole compositional analysis of gas in a geological formation through the use of spectroscopy.

2. State of the Art

Techniques for the qualitative and quantitative analysis of gas, liquid, and solid samples are well known. For example, as disclosed in U.S. Pat. No. 4,620,284 to R. P. Schnell, a helium-neon laser is used to provide photons of a 0.633 micron wave length which are directed at a sample flowing through a pipeline in an oil refinery. The resulting Raman scattering (scattering of light by molecular excitation) which comprises scattered light at different wavelengths than the incident light is then measured, and the measured spectrum is compared with previously obtained reference spectra of a plurality of substances.

In U.S. Pat. No. 4,609,821 to C. F. Summers, especially prepared rock cutting containing at least oil from an oil-based mud are excited with UV radiation with a 0.26 micron wave length. Instead of measuring the Raman spectrum as is done in the aforementioned Schnell patent, in accord with the Summers disclosure, the frequency and intensity of the resulting excited waves (fluorescence) which are at a longer wavelength than the incident radiation are detected and measured. By comparing the fluorescent spectral profile of the detected waves with similar profiles of the oil used in the oil-based mud, a determination is made as to whether formation oil is also found in the rock cuttings.

While the Summers and Schnell disclosures may be useful in certain limited areas, it will be appreciated that they suffer from various drawbacks. For example, the use of laser equipment in Schnell severely restricts the environment in which the apparatus may be used, as lasers are not typically suited to harsh temperature and/or pressure situations (e.g., a borehole environment). Also, the use of the Raman spectrum in Schnell imposes the requirement of equipment which can detect with very high resolution the low intensity scattered signals. The use by Summers of light having a 0.26 micron wavelength severely limits the investigation of the sample to a sample of nominal thickness. In fact, the Summers patent, while enabling a determination of whether the mud contains formation oil, does not permit an analysis of formation fluids in situ, and has no sensitivity to water.

Those skilled in the art will appreciate that the ability to conduct an analysis of formation fluids downhole is extremely desirable. With that in mind, the assignee of this application has provided a commercially successful borehole tool, the MDT (a trademark of Schlumberger) which extracts and analyzes a flow stream of fluid from a formation in a manner substantially as set forth in co-owned U.S. Pat. No. 3,859,851 to Urbanosky U.S. Pat. No. 3,780,575 to Urbanosky which is hereby incorporated by reference herein in its entirety. The OFA (a trademark of Schlumberger), which is a module of the MDT, determines the identity of the fluids in the MDT flow stream and quantifies the oil and water content based on the previously incorporated related patents. In particular, previously incorporated U.S. Pat. No. 4,994,671 to Safinya et al. provides a borehole apparatus which includes a testing chamber, means for directing a sample of fluid into the chamber, a light source preferably emitting near infrared rays and visible light, a spectral detector, a data base means, and a processing means. Fluids drawn from the formation into the testing chamber are analyzed by directing the light at the fluids, detecting the spectrum of the transmitted and/or backscattered light, and processing the information accordingly (and preferably based on the information in the data base relating to different spectra), in order to quantify the amount of water, gas, and oil in the fluid. As set forth in previously incorporated U.S. Pat. No. 5,266,800 to Mullins, by monitoring optical absorption spectrum of the fluid samples obtained over time, a determination can be made as to when a formation oil is being obtained as opposed to a mud filtrate. Thus, the formation oil can be properly analyzed and quantified by type. Further, as set forth in the previously incorporated U.S. Pat. No. 5,331,156 to Hines et al., by making optical density measurements of the fluid stream at certain predetermined energies, oil and water fractions of a two-phase fluid stream may be quantified.

While the Safinya et al., Mullins, and Hines et al. patents represent great advances in downhole fluid analysis, and are particularly useful in the analysis of oils and water present in the formation, they do not address in detail the gases which may be plentiful in the formation. The issue of in situ gas quantification is addressed in the previously incorporated U.S. Pat. Nos. 5,167,149 to Mullins et al., and 5,201,220 to Mullins et al., and in O. C. Mullins et al., "Effects of high pressure on the optical detection of gas by index-of-refraction methods", *Applied Optics*, Vol. 33, No. 34, pp. 7963–7970 (Dec. 1, 1994) which is also incorporated by reference herein in its entirety, where a rough estimate of the quantity of gas present in the flow stream can be obtained by providing a gas detection module having a detector array which detects light rays having certain angles of incidence. While rough estimates of gas quantities are helpful, it will be appreciated that compositional analysis of the gas would be more useful. In particular, gas analysis can be useful in determining which zones of a formation to produce, as gas zones with higher hydrocarbon content and with higher BTU content are more valuable than gas zones with lesser hydrocarbon content. In addition, it would be advantageous to be able to control the BTU content of the gas being produced without undergoing gas separation and recombination uphole, but rather by controlling quantities being produced from different locations in the borehole with advance knowledge of their respective BTU contents. Furthermore, downhole gas analysis could reveal the presence of noxious gases such as $H_2S$. Since $H_2S$ is reactive with logging tool metals and is also reactive with basic materials contained in water based mud filtrate, analysis of samples carried to the surface often underestimate the noxious gas content of the samples.

While techniques such as chromatography are routinely used for the analysis of gas in laboratories, the use of gas chromatography downhole is impractical due to several reasons. First, gas chromatography requires the use of a carrier gas flow stream whose volume far exceeds the sample gas volume. The handling of carrier gas within closed volumes of wireline tools represents a major problem especially considering that the formation gas pressures far exceed typical operating pressures of gas chromatography equipment. Second, handling of sample gas in gas chromatography equipment is difficult as very small volumes are used, and it is difficult to collect and transfer such small volumes from a large flow stream and guarantee representative samples. Third, the standard detectors for hydrocarbons in gas chromatography are a flame ionization detector and a thermal detector, both of which are impractical downhole because of the requirement of the maintenance of a stable flame downhole, and the wide variation in temperatures downhole. Finally, gas chromatography requires discrete measurements lasting several minutes which is undesirable in wireline applications. On the other hand, while spectroscopy has been used downhole for distinguishing between oil and water (in the near infrared spectrum), and for distinguishing among oils (in the visible spectrum), downhole spectroscopy has not been suggested for distinguishing between different hydrocarbon gases such as methane ($CH_4$), ethane (having methyl components ($CH_3$)), and higher hydrocarbons which contain methylene ($CH_2$) for several reasons. First, because the density of a gas is a function of pressure, and because downhole pressures can vary by a factor of thirty or more, the dynamic range of the gas densities likely to be encountered downhole is extremely large. As a result, the dynamic range of the spectral absorption at frequencies of interest is also extremely large such as to make a measurement unfeasible; i.e., the sensitivity of the downhole spectroscopy equipment is typically incapable of handling the large dynamic ranges that are encountered. Second, due to fact that the condensed phase of hydrocarbon (oil) has a much higher density at downhole pressures than the gas phase, a thin film of liquid on the OFA window can yield significant absorption. Thus, interpretation of the results would yield a determination of a rich gas mixture, where no or little amounts of hydrocarbon gas was actually present. Third, the type of spectral analysis typically done uphole to distinguish among hydrocarbon gases cannot be done downhole. In particular, in uphole applications, individual gas constituents are detected by modulating a narrow band source on and off of mid-infrared absorption lines of the gas, where a resulting oscillation in absorption at each modulation frequency would indicate a positive detection of a particular gas. However, at the high pressures encountered downhole, not only are the narrow gas absorption spectral lines merged, but mid-infrared spectroscopy is hindered by the extreme magnitude of the absorption features. Fourth, spectrometers are typically sensitive to changes in temperature, and elevated temperatures encountered downhole can induce spectral changes of the gas sample, thereby complicating any data base utilized.

SUMMARY OF THE INVENTION

It is therefore an object of the invention to provide downhole apparatus and methods for quantitatively analyzing the composition of formation gases.

It is another object of the invention to provide apparatus and methods for quantitatively analyzing hydrocarbon gases downhole using spectroscopy techniques.

It is a further object of the invention to provide apparatus and methods which overcome dynamic range issues and permit spectral analysis downhole for quantitatively analyzing formation gases.

It is an additional object of the invention to provide apparatus and methods which overcome other problems previously encountered in using spectral analysis downhole to quantitatively analyze formation gases.

Another object of the invention is to provide apparatus and methods for quantitatively analyzing formation gases for BTU content.

In accord with the objects of the invention, a downhole apparatus for analyzing formation gases is provided and generally comprises means for obtaining a flow of formation and borehole fluids through a path in the downhole apparatus, means for analyzing the obtained formation and/or borehole fluids for the presence of gas, diverter means for diverting formation gas into a separate stream, and a gas analysis module for analyzing the formation gas in that stream. According to the preferred embodiment of the invention, the gas analysis module includes a light source, a plurality of photo-detectors, a gas sample cell (or cells) having a plurality of portions with different path lengths and with a plurality of windows, and a fiber optic bundle for directing light from the light source to some of the windows, and from others of the windows to the photo-detectors. For example, a gas sample cell or cells preferably includes a portion with a 2 mm path length, another portion with a 4 mm path length, and a third portion with a 10 mm path length. If desired, pressure sensing means may be provided for controlling which optical information is provided to the photo-detectors. Alternatively, separate photo-detectors can be provided for each of the cells having different path lengths.

By providing a diverter means and a separate gas analysis module, the likelihood of having a thin film of oil on the cell window is decreased substantially, thereby improving analysis results. Also, by providing one or more cells with different path lengths, issues of dynamic range are obviated, because where the pressure is higher, light will not be fully absorbed in the cell having a short path length, whereas where the pressure is lower, there will be some absorption in the cell having the longer path length. Thus, spectral analysis of gas will be possible downhole.

According to another aspect of the invention, the gas analysis module is provided with a first optical path from the light source to the photo-detectors which goes through the cell or cells, a second optical path which goes directly from the light source to the photo-detectors, and third a optical path which goes from the light source, through a known standard to the photo-detectors. The known standard is preferably a natural gas with a known BTU content such as methane, although other standards could be utilized. The provision of the second path, which is known in the art, is used to cancel drift in the light source, detector, and electronics in order to provide a more robust spectral measurement. The provision of the third path through a known standard permits compensation for shifts in actual hydrocarbon peak locations or shifts in optical filter wavelengths, yielding an even more robust determination of sample properties in the downhole environment.

In accord with yet another aspect of the invention, analysis of the different hydrocarbon gas components of the gas stream is conducted by analysis of selected CH vibrational peaks in the near infrared range (NIR) of 4000–10,000 $cm^{-1}$ (as opposed to the mid-range used uphole), and preferably, specifically, particular peaks in the 5700 $cm^{-1}$ to 6100 $cm^{-1}$ range. Thus, one or more optical filters are preferably provided in conjunction with the gas analysis module so that extraneous wavelengths outside of the desired range are not received at the photo-detectors.

Additional objects and advantages of the invention will become apparent to those skilled in the art upon reference to the detailed description taken in conjunction with the provided figures.

BRIEF DESCRIPTION OF THE DRAWINGS

FIGS. 5c and 5d are plots of the NIR wavelength spectra at high pressures respectively of methane and heptane, and of n-heptane, n-nonane, and n-hexadecane.

DETAILED DESCRIPTION OF THE PREFERRED EMBODIMENTS

Figure 1:
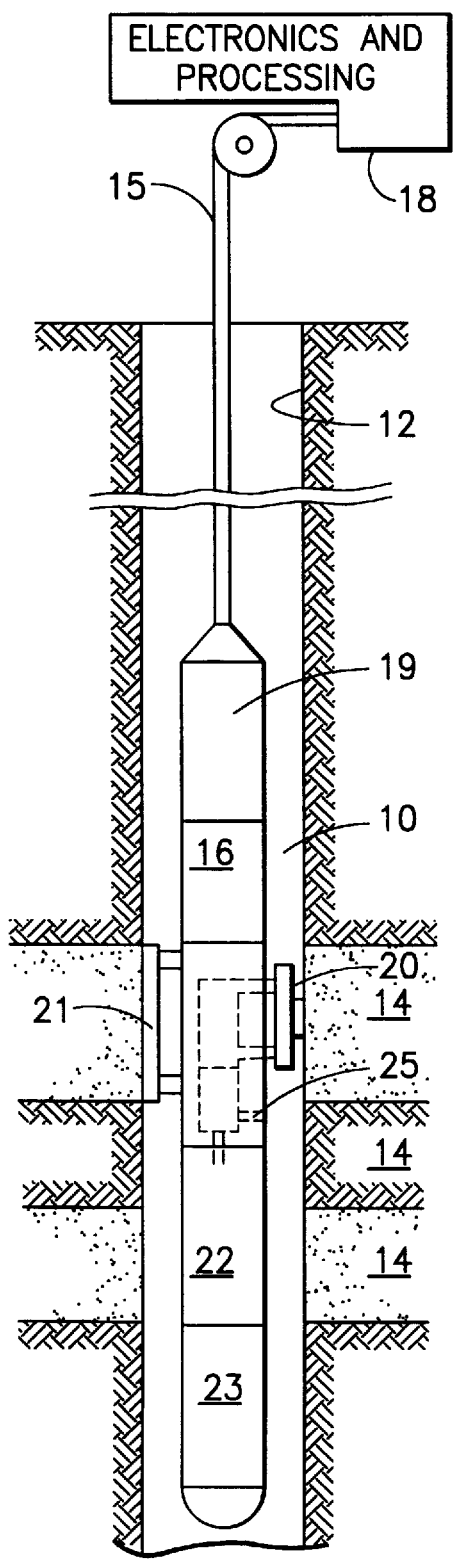
FIG. 1 is a schematic diagram of a borehole apparatus for analyzing formation fluids.

The instant invention is particularly applicable to both production logging and to borehole investigative logging. For purposes of brevity, however, the description herein will be primarily directed to borehole investigative logging, and the terms "borehole" and "borehole tool" should be read throughout the specification and claims to encompass a (cased) well and a tool used in a well, as well as in a borehole. Thus, a borehole tool 10 for testing earth formations and analyzing the compositions of fluids from the formation 14 in accord with the invention is seen in FIG. 1. As illustrated the tool 10 is suspended in the borehole 12 from the lower end of a typical multiconductor cable 15 that is spooled in a usual fashion on a suitable winch (not shown) on the formation surface. On the surface, the cable 15 is preferably electrically coupled to an electrical control system 18. The tool 10 includes an elongated body 19 which encloses the downhole portion of the tool control system 16. The elongated body 19 also carries a selectively extendable fluid admitting assembly 20 and a selectively extendable tool anchoring member 21 which are respectively arranged on opposite sides of the body. The fluid admitting assembly 20 is equipped for selectively sealing off or isolating selected portions of the wall of borehole 12 such that pressure or fluid communication with the adjacent earth formation is established. Also included with tool 10 are a fluid analysis module 25 through which the obtained fluid flows. The fluid may thereafter be expelled through a port (not shown) or it may be sent to one or more fluid collecting chambers 22 and 23 which may receive and retain the fluids obtained from the formation. Control of the fluid admitting assembly, the fluid analysis section, and the flow path to the collecting chambers is maintained by the electrical control systems 16 and 18.

Additional details of methods and apparatus for obtaining formation fluid samples may be had by reference to U.S. Pat. No. 3,859,851 to Urbanosky and U.S. Pat. No. 4,396,259 to Miller which are hereby incorporated by reference herein. It should be appreciated, however, that it is not intended that the invention be limited to any particular method or apparatus for obtaining the formation fluids.

Figure 2:
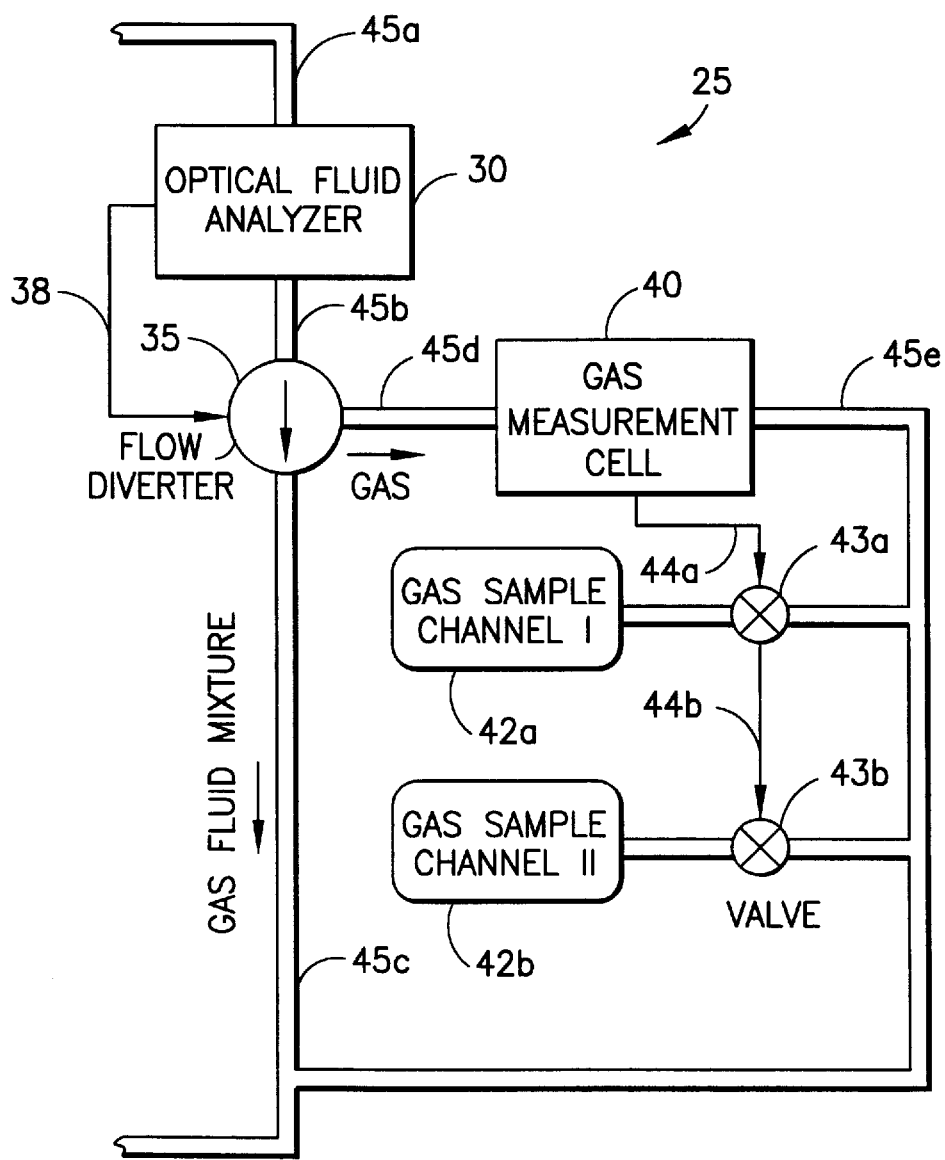
FIG. 2 is a schematic diagram of the preferred fluid analysis module of FIG. 1.

Turning to FIG. 2, a schematic diagram is seen of the preferred fluid analysis module 25 of FIG. 1. As seen in FIG. 2, the fluid analysis module 25 includes an optical fluid analyzer 30, a flow diverter 35 with associated control line 38, a gas measurement cell 40, optional gas sample chambers 42a and 42b with associated valves 43a, 43b and control lines 44a, 44b, and gas and fluid flow lines 45a, 45b, 45c, 45d, and 45e. The optical fluid analyzer 30, which receives fluids from the borehole and formation via fluid flow line 45a is preferably an analyzer such as shown and described in previously incorporated U.S. Pat. No. 4,994, 671 to Safinya et al., No. 5,167,149 to Mullins et al., 5,201,220 to Mullins et al., No. 5,266,800 to Mullins et al., and No. 5,331,156 to Hines et al. Thus, the optical fluid analyzer 30 is capable of distinguishing between oil, water, and gas, and as set forth in U.S. Pat. No. 5,167,149 to Mullins et al., and U.S. Pat. No. 5,201,220 to Mullins et al., is capable of categorizing the fluid sample as high gas, medium gas, low gas, and no gas. When the fluid sample contains oil or water, the fluid sample is either optionally stored in sample fluid chambers (not shown), or expelled back into the borehole via fluid flow lines 45b and 45c.

According to the preferred embodiment of the invention, upon determining that the fluid sample is substantially all gas (i.e., the fluid sample has a high gas content), the fluid analyzer 30 provides a control signal via control line 38 to the flow diverter which diverts the fluid sample via flow line 45d to the gas measurement cell 40 for analysis. While the flow diverter 35 can take many forms, preferably, it is simply embodied as an electronically controlled 2-way valve. After passing through the gas measurement cell 40, the gas may be sent to one or more gas sample chambers 43a, 43b, for storage. Valves 43a, 43b under control of the gas measurement cell 40 via control lines 44a, 44b are provided for that purpose. Alternatively, the gas may be passed via fluid flow line 45e back to fluid flow line 45c for the purpose of being expelled back into the borehole. If desired, backflow or check valves (not shown) may be provided to prevent borehole fluids from backing back into flow line 45d.

Figure 3:
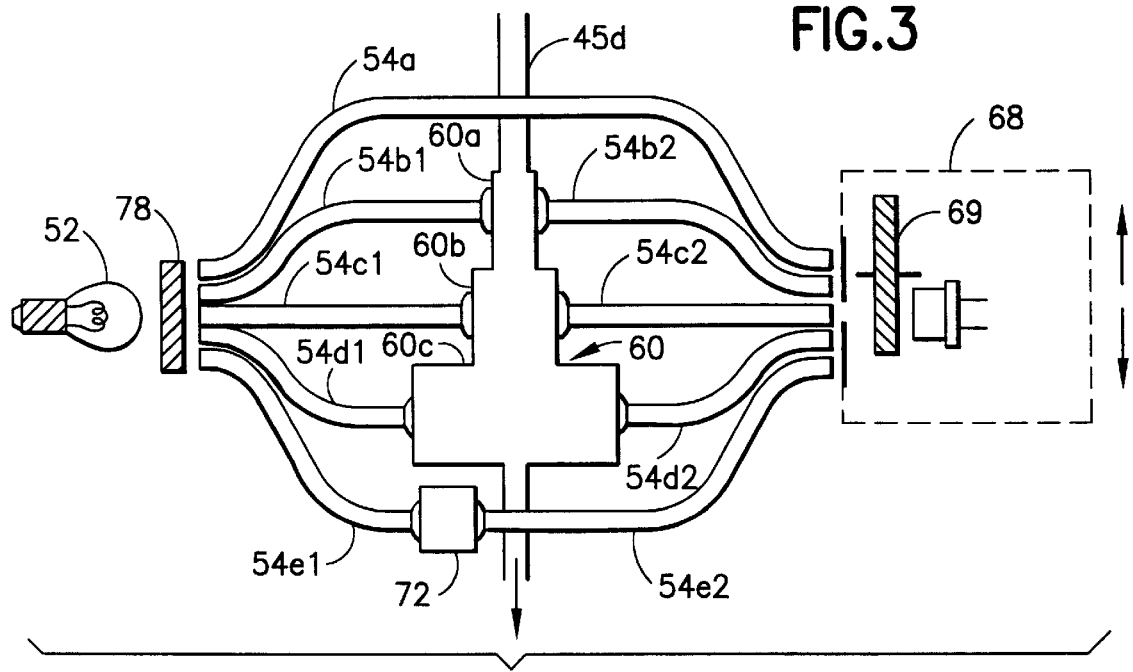
FIGS. 3 and 4 are schematic diagrams of first and second embodiments of the gas measurement cell of FIG. 2.

Details of a first embodiment of the gas measurement cell 40 are seen in FIG. 3 where the cell 40 is seen to include a light source 52, a fiber optic bundle(s) 54 (with portions 54a, 54b1, 54b2, 54c1, 54c2, 54d1, 54d2, 54e1 and 54e2), a variable path length vessel 60, including portions 60a, 60b, and 60c, a photo-detector means 68, and a known sample 72. As indicated, gas received via control line 45d is provided to the vessel 60 which includes portion 60a having a 2 mm path length (width), portion 60b having a 4 mm path length, and portion 60c having a 10 mm path length. The vessel 60 includes windows (not shown) through which the light is directed. The light is obtained from the light source 52 which preferably provides light in the near infrared (NIR) spectrum. If desired, an optical filter 78 may be provided at the light source to filter out light of other wavelengths. Regardless, light from the light source 52 is carried via optical fibers 54b1, 54c1, and 54d1 to the vessel 60, and light emerging from the vessel is carried by optical fibers 54b2, 54c2, and 54d2 to the photo-detector means 68. The photo-detector means 68 preferably includes several arrays of photo-detectors tuned to different frequencies of interest (as discussed below), but may include only a single photo-detector in conjunction with a filter wheel which permits a time division multiplexed determination of the frequency spectrum of the sample flowing through the vessel. Furthermore, it will be appreciated that, the light emerging from each of the portions 60a, 60b, and 60c may be sensed by different sets of photo-detectors, or as shown in FIG. 3, may be time division multiplexed to a single set of the photo-detectors through an aperture 81 which moves in conjunction with the entire photo-detector means 68. If desired, pressure sensing means may be provided for controlling which optical information is provided to the photo-detectors, as the cell portion having an appropriate path length for sensing the gas and providing a reading in a desired range will often be a function of pressure; i.e., the gas density (and hence absorbance per unit path length) varies as a function of pressure. In any event, it is generally preferable that the light provided to the photo-detector means 68 via fibers 54b2, 54c3, and 54d2 be separately sensed, because where the density of the gas is low, the light emerging from sample portion 60c may provide a desirable signal, but the light emerging from sample portion 60a will be too large and will not permit an appropriate analysis.

As previously mentioned, light from the light source is also carried by fibers 54a for detection by the photo-detector means 68, and by fibers 54e1 to the known reference sample 72, and from the reference sample by fibers 54e2 to the photo-detector means 68. The provision of fibers 54a for carrying light directly to the photo-detector means 68 is known in the art, and is used to cancel drift in the light source, detector, and electronics in order to provide a more robust spectral measurement. The provision of a third path through the known sample 72, however, permits compensation for shifts in actual hydrocarbon peak locations or shifts in optical filter wavelengths, yielding an even more robust determination of sample properties in the downhole environment. In particular, the known sample is preferably a natural gas (such as methane) with a known BTU content, although other known samples such as plastic films or methane clathrates or adducts can be utilized. With the known sample, shifts in actual hydrocarbon peak locations (discussed below) or shifts in optical filter wavelengths can be easily determined, thus permitting a relatively straight-forward compensation for the unknown sample being analyzed.

Figure 4:
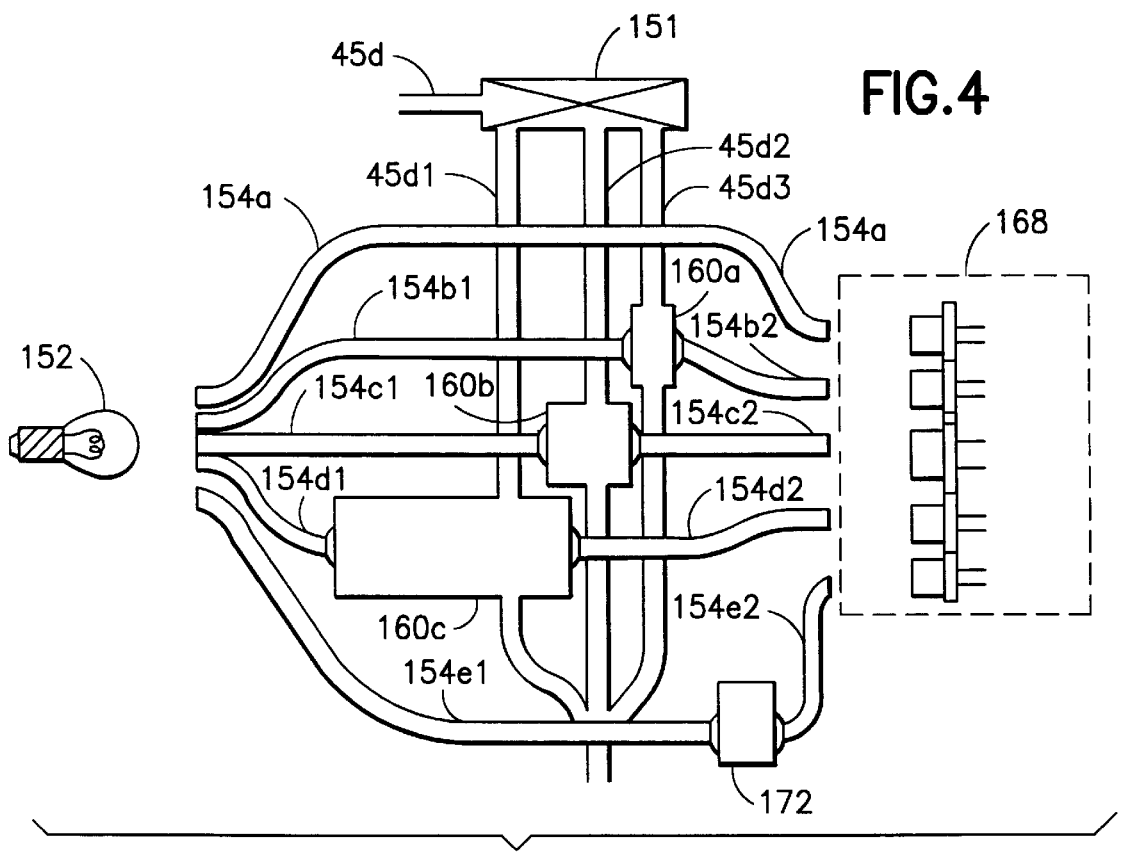

Turning to FIG. 4, a second embodiment of the gas measurement cell 40 which is similar to the embodiment of FIG. 3 is seen (with like or similar elements indicated by similar numerals increased by 100) where the cell 40 includes a diverter(s) 151, a light source 152, a fiber optic bundle(s) 154 (with portions 154a, 154b1, 154b2, 154c1, 154c2, 154d1, 154d2, 154e1 and 154e2), vessels 160a, 160b, 160c of different path width, a photo-detector means 168, and a known sample 172. As indicated, gas received via control line 45d is diverted to lines 45d1, 45d2 and 45d3 and provided to the three separate vessels 160a, 160b, 160c. Vessel 160a preferably has a 2 mm path length (width), with vessel 160b preferably having a 4 mm path length, and vessel 160c preferably having a 10 mm path length. Each vessel includes windows (not shown) through which the light is directed. The light is obtained from the light source 152 which preferably provides light in the near infrared (NIR) spectrum. The NIR light from the light source 152 is carried via optical fibers 154b1, 154c1, and 154d1 to the vessels 160a, 160b, and 160c respectively, and light emerging from the vessels is carried by optical fibers 154b2, 154c2, and 154d2 to a photo-detector means 168 which is comprised of several arrays of photo-detectors tuned to different frequencies of interest. A microprocessor (not shown) coupled to the sample photo-detector arrays is utilized to determine from which one or more of the arrays the frequency spectrum information is to be used. Light from the light source is also carried by fibers 154a to the photo-detector means 168, and by fibers 154e1 to the known sample 172, and from the reference sample by fibers 154e2 to the photo-detector means 168. If desired, separate photo-detectors means (not shown) can be provided for detecting light from fibers 154a and 154e2.

Figure 5A:
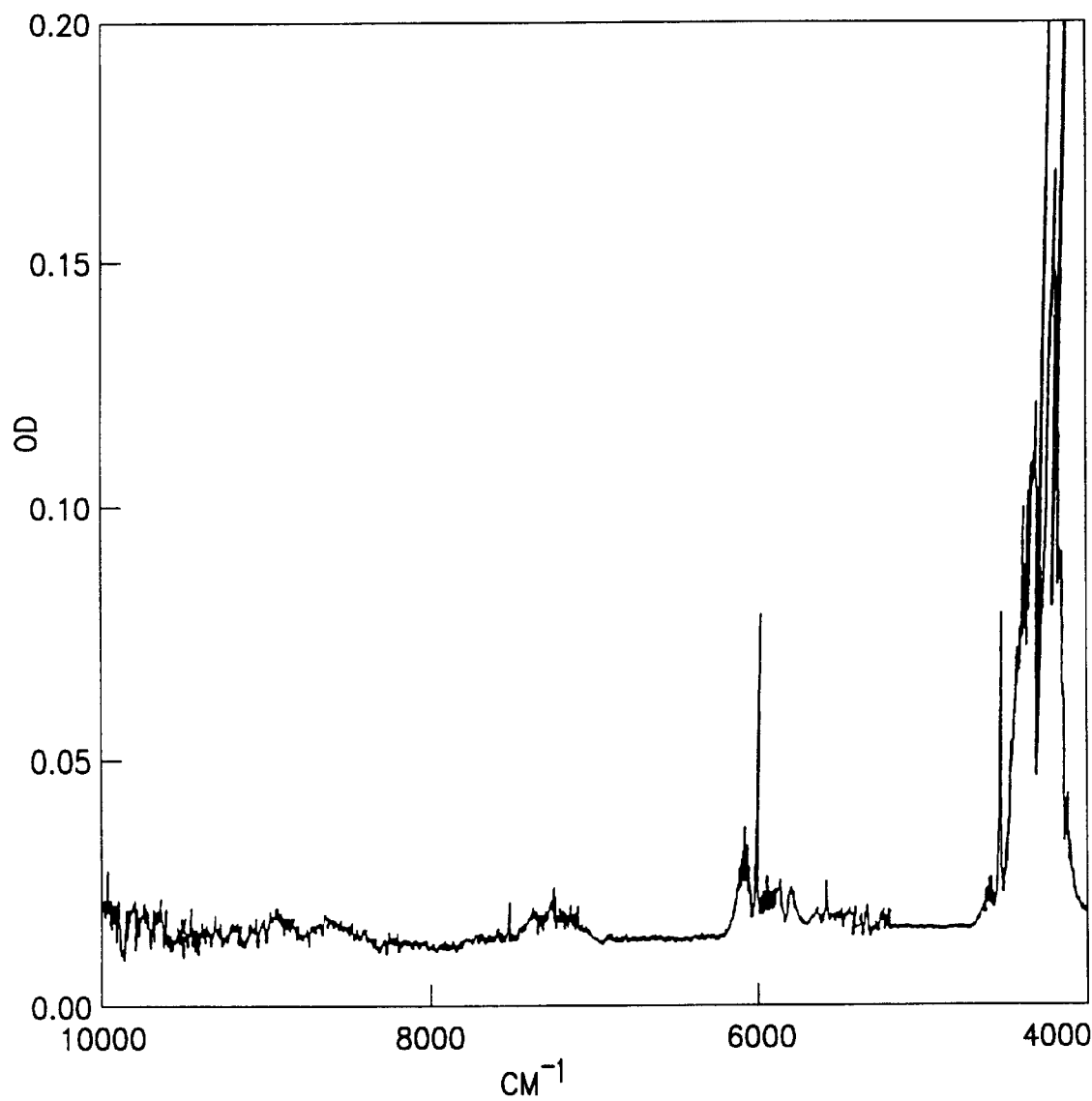
FIGS. 5a and 5b are optical density versus near infrared wavelength spectra of methane at low pressure, low temperature, and a high pressure, high temperature respectively.
Figure 5B:
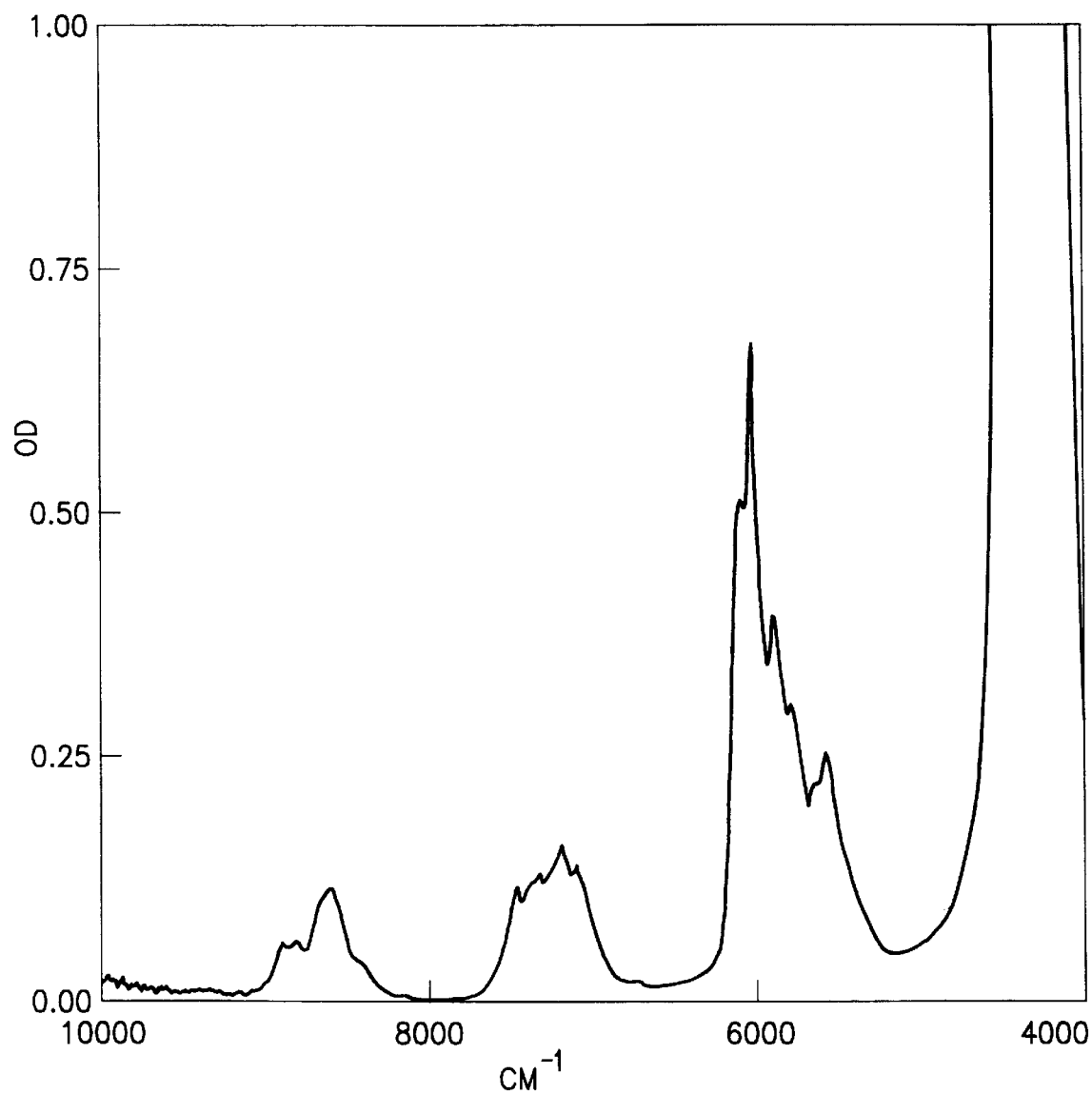

In accord with yet another aspect of the invention, analysis of the different hydrocarbon gas components of the gas stream is conducted by analysis of selected CH vibrational peaks in the near infrared range (NIR) of 4000–10,000 cm$^{-1}$, and preferably, specifically, particular peaks in the 5780 cm$^{-1}$ to 6020 cm$^{-1}$ range. More particularly, as seen in FIG. 5a, a low pressure low temperature optical density versus wavelength spectrum (e.g., ambient uphole T and P) of methane is seen. The high temperature (T=204° C.), high pressure (P=10,000 psi) spectrum typical of downhole environments is seen in FIG. 5b. Comparing the two spectra, it is clear that the optical densities are much greater and much less defined (i.e., the peaks are spread) at the high pressures. In fact, the peaks around 6000 cm$^{-1}$ (representing the two-stretch overtone), which in the low P, low T spectrum have optical densities of below 0.10, are very useful in the high P, high T situations. Alternatively, even peaks in the 7000 cm$^{-1}$ and 8600 cm$^{-1}$ ranges can be utilized at high pressures. Where high pressures are encountered, instead of utilizing vessels or cells of different path widths, it is possible to shift the frequency analysis to the different NIR peaks.

Figure 5C:
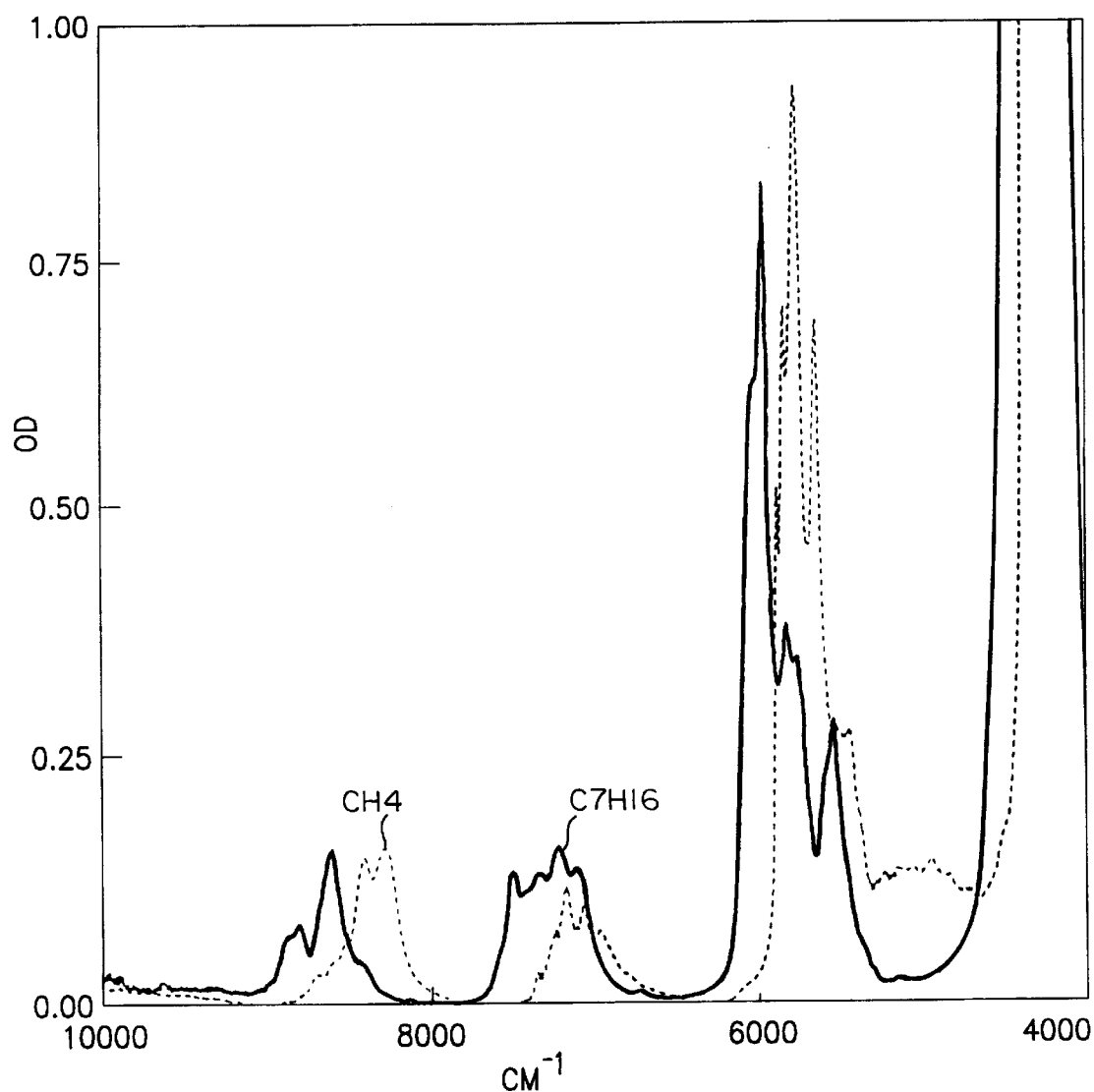

Turning to FIG. 5c, a comparison of the NIR spectra of methane and heptane at high pressures (about 10,000 psi) is seen. The methane ($CH_4$) shows shifted peaks compared to the heptane, which includes $CH_3$ and $CH_2$ groups (e.g., compare the two-stretch peak of methane at 6000 cm$^{-1}$ against the two-stretch peak of heptane at about 5806 cm$^{-1}$ which is a composite of the two-stretch $CH_2$ peak at about 5782 cm$^{-1}$, and the two-stretch $CH_3$ peaks at 5871 cm$^{-1}$ and 5911 cm$^{-1}$). Also, turning to FIG. 5d, a comparison of the NIR spectra at between 5700 cm$^{-1}$ and 6000$^{-1}$ of the two-stretch overtones of n-heptane, n-nonane, and n-hexadecane (each having different $CH_2$ and $CH_3$ ratios) indicates that each has a peak at slightly different frequencies, and yields a slightly different optical density. Thus, it is evident that by obtaining a near infrared absorbance spectrum of a downhole gas at high temperatures and high pressures, a determination can be made as to the relative compositions of $CH_2$, $CH_3$, and $CH_4$ in the gas, and hence the BTU content of the gas.

Figure 6:
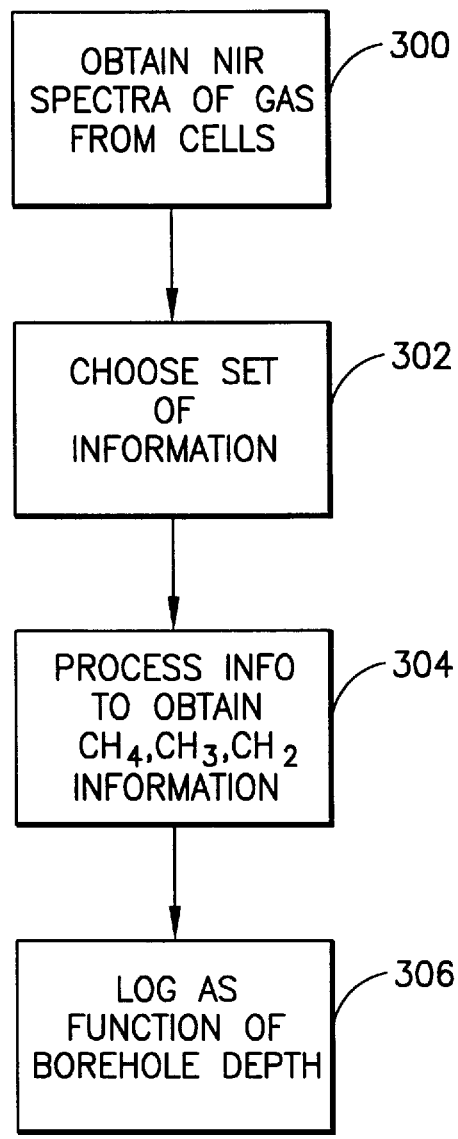
FIG. 6 is a flowchart of the method of the invention.

Turning to FIG. 6, a broad statement of the method of the invention is seen in flowchart format. At 300, the NIR absorbance spectra of gas from a plurality of optical cells are obtained, as well as spectra from a standard and from a sample. Based on the spectral information obtained, as well as any other information such as downhole pressure and temperature (if available), a microprocessor located either downhole or uphole, at 302, chooses which set or sets of information to process. At 304, the information is processed by fitting the data to known spectra which include $CH_2$, $CH_3$, and $CH_4$ information, while correcting for temperature and pressure effects (preferably utilizing the standard and sample spectra) in order to obtain information regarding amounts of $CH_2$, $CH_3$, and $CH_4$ in the gas stream. It will be appreciated that many different techniques can be used at step 304, including least mean squares fitting, multivariate analysis, etc. At 306, determinations relating to the gas content are logged as a function of depth in the borehole. These determinations which may include one or more of BTU content, and amounts of different hydrocarbons in the gas stream. The determinations may later be compared to actual gas samples obtained for confirmation purposes, and/or may be later used for production purposes to control the BTU content of a gas stream being produced from the well.

It should be appreciated that information regarding other gases in the flow stream such as $CO_2$ and $H_2S$ which show vibrational absorption in the NIR range may also be obtained using the techniques set forth above.

There have been described and illustrated herein apparatus and methods for the downhole compositional analysis of formation gases. While particular embodiments of the invention have been described, it is not intended that the invention be limited thereto, as it is intended that the invention be as broad in scope as the art will allow and that the specification be read likewise. Thus, while the invention has been described with reference to certain preferred apparatus for obtaining borehole and formation fluids, other apparatus could be utilized. Likewise, while certain preferred apparatus (the OFA) for determining when a flow stream has converted to substantially all gas has been described, other such apparatus could be utilized. In addition, while particular gas measurement cell arrangements were described, other arrangements could be utilized. Thus, instead of three cells or vessels of 2 mm, 4 mm, and 10 mm in width, different numbers of cells and/or different widths could be utilized advantageously. Also, while particular photo-detector arrangements were discussed, other spectral detector arrangements could be utilized. Further, instead of using both a direct path and a path through a known reference sample for correction, only the path through the known reference sample need be utilized. Further yet, while specific spectral peaks in the NIR spectrum (around 6000 $cm^{-1}$) were discussed as being preferred for hydrocarbon analysis, it will be appreciated that other NIR peaks could be utilized. It will therefore be appreciated by those skilled in the art that yet other modifications could be made to the provided invention without deviating from its spirit and scope as so claimed.

What is claimed is:

1. A borehole tool for investigating gases from a formation traversed by a borehole, comprising:

a) means for obtaining a stream of fluid from the formation, said stream of fluid comprising at any one time, at least one of gas, oil, water, and borehole mud;

b) means for determining when said stream of fluid is comprised of substantially all gas;

c) diverter means coupled to said means for obtaining and to said means for determining, said diverter means for diverting formation gas into a second stream separate from said stream of fluid when or after said means for determining determines that said fluid is comprised of substantially all gas; and d) means for determining indications of the composition of said formation gas in said second stream.

2. A borehole tool according to claim 1, wherein:

said means for determining indications includes a light source means for emitting rays in at least a portion of the near infrared (NIR) spectrum, a gas sample cell having at least one window through which said NIR rays from said light source means are directed, and spectral detector means for detecting the spectra of at least NIR rays which were at least one of scattered by and transmitted through said formation gases in said sample cell.

3. A borehole tool according to claim 2, wherein:

said gas sample cell includes a plurality of portions having different path lengths and a plurality of windows, said spectral detector means for detecting the spectra of said near infrared rays which were at least one of scattered by and transmitted through said formation gases in said sample cell at said plurality of portions.

4. A borehole tool according to claim 3, wherein:

said plurality of portions includes a first portion having a first path length, and a second portion having a second path length, said second path length being at least twice as long as said first path length.

5. A borehole tool according to claim 4, wherein:

said spectral detector means comprise a plurality of photo-detectors, at least one photo-detector for each of said plurality of portions.

6. A borehole tool according to claim 4, wherein:

said spectral detector means comprises a photo-detector, with said near infrared rays received via different of said plurality of portions being time division multiplexed to said photo-detector.

7. A borehole tool according to claim 2, wherein:

said means for determining indications includes at least one fiber optic bundle for directing light from said light source means to said gas sample cell, and from said gas sample cell to said spectral detector means.

8. A downhole apparatus for analyzing formation gases of a formation, comprising:

a) means for obtaining a stream of fluid from the formation, said stream of fluid including the formation gases;

b) gas sample cell means for receiving said formation gases downhole, said gas sample cell means having first and second portions of different widths, with said first portion having a first window, and said second portion having a second window;

c) light source means for emitting downhole at least rays in a portion of the near infrared spectrum towards said first and second windows of said gas sample cell means; and d) spectral detector means for detecting downhole the spectra of at least near infrared rays which were at least one of scattered by and transmitted through said formation gases in said portions of different widths of said gas sample cell means.

9. An apparatus according to claim 8, wherein:

said first portion has a first width, and said second portion has a second width, wherein said second width is at least twice as large as said first width.

10. An apparatus according to claim 9, wherein:

said gas sample cell means includes a third portion having a third width.

11. An apparatus according to claim 9, wherein:

said first portion comprises a first vessel, and said second portion comprises a second vessel, wherein formation gases moving through said first vessel do not move through said second vessel.

12. An apparatus according to claim 9, wherein:

said first portion and said second portion are substantially adjacent, and formation gases moving through said first portion move through said second portion.

13. An apparatus according to claim 9, further comprising:

e) at least one fiber optic bundle for directing light from said light source means to said gas sample cell means, and from said gas sample cell means to said spectral detector means.

14. A downhole apparatus for analyzing formation gases of a formation, comprising:

a) means for obtaining a stream of fluid from the formation, said stream of fluid including the formation gases under downhole pressures of at least 1000 psi;

b) gas sample cell means for receiving said formation gases under downhole pressure;

c) light source means for emitting rays in at least a portion of the near infrared spectrum towards said gas sample cell means;

d) spectral detector means for detecting the spectrum of near infrared rays in a range of 5700 cm$^{-1}$ to 6100 cm$^{-1}$ which were at least one of scattered by and transmitted through said formation gases in said gas sample cell means under said downhole pressures;

e) processing means coupled to said spectral detector means, said processing means for using said spectrum detected by said spectral detector means, and for using indications of known spectra of a plurality of different hydrocarbon gases under downhole pressures of at least 1000 psi to determine indication of at least one of (i) a BTU content of said formation gases and (ii) quantities of said plurality of different hydrocarbon gases.

15. An apparatus according to claim 14, wherein:

said gas sample cell includes a plurality of portions having different path lengths and a plurality of windows, said spectral detector means for detecting the spectra of said near infrared rays which were transmitted through said formation gases in said sample cell at said plurality of portions.

16. An apparatus according to claim 14, wherein:

said indications of known spectra include indications which include a two-stretch peak of methane at substantially 6000 cm$^{-1}$, a two-stretch peak of CH$_2$ peak at about 5782 cm$^{-1}$, and two-stretch peaks of CH$_3$ at 5871 cm$^{-1}$ and 5911 cm$^{-1}$.

17. A downhole apparatus for analyzing formation gases of a formation, comprising:

a) means for obtaining a stream of fluid from the formation, said stream of fluid including the formation gases;

b) gas sample cell means for receiving said formation gases;

c) a gas sample of known hydrocarbon content;

d) light source means for emitting downhole at least near infrared rays towards said gas sample cell means and toward said known sample;

e) spectral detector means for detecting downhole the spectra of at least near infrared rays which were at least one of scattered by and transmitted through said formation gases and through said gas sample; and f) processing means coupled to said spectral detector means, said processing means for using said spectra in analyzing at least one of a BTU content of the formation gases and quantities of a plurality of different hydrocarbon gases in the formation gases.

18. An apparatus according to claim 17, further comprising:

f) fiber optic bundle means for directing light from said light source means to said gas sample cell means and to said gas sample of known hydrocarbon content, and from said gas sample cell means and said gas sample of known hydrocarbon content to said spectral detector means.

19. An apparatus according to claim 18, wherein:

said fiber optic bundle means also directs light from said light source means directly to said spectral detector means.

20. A method for determining indications of the composition of gases from a formation, comprising:

a) at pressures of at least 1000 psi, obtaining indications of the absorbance spectrum of the formation gases downhole in at least a portion of the near infrared spectrum;

b) using said indications as well as indications of the absorbance spectrum in said portion of the near infrared spectrum of CH$_4$, CH$_3$, and CH$_2$, to determine indications of the composition of said formation gases.

* * * * *